US007709557B2

(12) United States Patent  
Medoff et al.

(10) Patent No.: US 7,709,557 B2
(45) Date of Patent: May 4, 2010

(54) COMPOSITIONS AND COMPOSITES OF CELLULOSIC AND LIGNOCELLULOSIC MATERIALS AND RESINS, AND METHODS OF MAKING THE SAME

(75) Inventors: Marshall Medoff, Brookline, MA (US); Arther P. Lagace, Newtonville, MA (US)

(73) Assignee: Xyleco, Inc., Woburn, MA (US)

( * ) Notice: Subject to any disclaimer, the term of this patent is extended or adjusted under 35 U.S.C. 154(b) by 0 days.

(21) Appl. No.: 12/422,665

(22) Filed: Apr. 13, 2009

(65) Prior Publication Data

US 2009/0250179 A1 Oct. 8, 2009

Related U.S. Application Data

(60) Continuation of application No. 12/040,275, filed on Feb. 29, 2008, now abandoned, which is a division of application No. 10/994,846, filed on Nov. 22, 2004, now abandoned, which is a division of application No. 10/336,972, filed on Jan. 6, 2003, now abandoned, which is a continuation-in-part of application No. 10/104,414, filed on Mar. 21, 2002, now abandoned.

(51) Int. Cl.
C08J 3/00 (2006.01)
C08J 3/20 (2006.01)
C08L 1/00 (2006.01)
C08L 99/00 (2006.01)
A01N 25/00 (2006.01)

(52) U.S. Cl. .................. 523/129; 524/13; 524/14; 524/76

(58) Field of Classification Search .......... 523/129; 524/13, 14, 76
See application file for complete search history.

(56) References Cited

U.S. PATENT DOCUMENTS

| 1,824,221 | A | 9/1931 | Mason |
| 2,516,847 | A | 8/1950 | Boehm |
| 2,519,442 | A | 8/1950 | Delorme et al. |
| 2,558,378 | A | 6/1951 | Petry |
| 2,635,976 | A | 4/1953 | Meiler et al. |
| 2,658,828 | A | 11/1953 | Pattilloch |
| 2,665,261 | A | 1/1954 | Baker |
| 2,680,102 | A | 6/1954 | Becher |
| 2,757,150 | A | 7/1956 | Heritage |
| 2,789,903 | A | 4/1957 | Lukman et al. |
| 2,935,763 | A | 5/1960 | Newman et al. |
| 3,308,218 | A | 3/1967 | Wiegand et al. |
| 3,309,444 | A | 3/1967 | Schueler |
| 3,493,527 | A | 2/1970 | Schueler |
| 3,516,953 | A | 6/1970 | Wood |
| 3,596,314 | A | 8/1971 | Krugler |
| 3,645,939 | A | 2/1972 | Gaylord |
| 3,671,615 | A | 6/1972 | Price |
| 3,697,364 | A | 10/1972 | Boustany |
| 3,709,845 | A | 1/1973 | Boustany |
| 3,718,536 | A | 2/1973 | Downs et al. |
| 3,836,412 | A | 9/1974 | Boustany et al. |
| 3,878,143 | A | 4/1975 | Baumann et al. |
| 3,888,810 | A | 6/1975 | Shinomura |
| 3,943,079 | A | 3/1976 | Hamed |
| 3,956,541 | A | 5/1976 | Pringle |
| 3,956,555 | A | 5/1976 | McKean |
| 4,005,162 | A | 1/1977 | Bucking |
| 4,016,232 | A | 4/1977 | Pringle |
| 4,033,913 | A | 7/1977 | Sunden |
| 4,045,603 | A | 8/1977 | Smith |
| 4,056,591 | A | 11/1977 | Goettler et al. |
| 4,058,580 | A | 11/1977 | Flanders |
| 4,097,648 | A | 6/1978 | Pringle |
| 4,112,038 | A | 9/1978 | Garner |
| 4,113,908 | A | 9/1978 | Shinomura |
| 4,115,497 | A | 9/1978 | Halmo et al. |
| 4,145,389 | A | 3/1979 | Smith |
| 4,168,251 | A | 9/1979 | Schinzel et al. |
| 4,187,352 | A | 2/1980 | Klobbie |
| 4,203,876 | A | 5/1980 | Dereppe et al. |
| 4,204,010 | A | 5/1980 | Kramm et al. |
| 4,228,116 | A | 10/1980 | Colombo et al. |
| 4,239,679 | A | 12/1980 | Rolls et al. |
| 4,244,847 | A | 1/1981 | Posiviata et al. |
| 4,244,903 | A | 1/1981 | Schnause |
| 4,248,743 | A | 2/1981 | Goettler |
| 4,248,820 | A | 2/1981 | Haataja |
| 4,250,222 | A | 2/1981 | Mavel et al. |

(Continued)

FOREIGN PATENT DOCUMENTS

AU 47811/90 1/1989

(Continued)

OTHER PUBLICATIONS

Dalvag et al., "The Efficiency of Cellulosic Fillers in Common Thermoplastics. Part II. Filling with Process Aids and Coupling Agents", International Journal of Polymeric Materials, 1985, vol. 11, pp. 9-38.

(Continued)

*Primary Examiner*—Nathan M Nutter
(74) *Attorney, Agent, or Firm*—Celia H. Leber

(57) ABSTRACT

Cellulosic or lignocellulosic materials, and compositions and composites made therefrom, are disclosed.

26 Claims, 3 Drawing Sheets

U.S. PATENT DOCUMENTS

| | | |
|---|---|---|
| 4,263,184 A | 4/1981 | Leo et al. |
| 4,265,846 A | 5/1981 | Shen et al. |
| 4,273,688 A | 6/1981 | Porzel et al. |
| 4,277,428 A | 7/1981 | Luck et al. |
| 4,279,790 A | 7/1981 | Nakajima |
| 4,281,039 A | 7/1981 | Miura et al. |
| 4,290,988 A | 9/1981 | Nopper et al. |
| 4,303,019 A | 12/1981 | Haataja et al. |
| 4,305,901 A | 12/1981 | Prince et al. |
| 4,311,554 A | 1/1982 | Herr |
| 4,311,621 A | 1/1982 | Nishizawa et al. |
| 4,318,351 A | 3/1982 | Munk |
| 4,323,625 A | 4/1982 | Coran et al. |
| 4,328,136 A | 5/1982 | Blount |
| 4,376,144 A | 3/1983 | Goettler |
| 4,382,108 A | 5/1983 | Carroll et al. |
| 4,393,020 A | 7/1983 | Li et al. |
| 4,414,267 A | 11/1983 | Coran et al. |
| 4,420,351 A | 12/1983 | Lussi et al. |
| 4,426,470 A | 1/1984 | Wessling et al. |
| 4,433,813 A | 2/1984 | Whatton et al. |
| 4,440,708 A | 4/1984 | Haataja et al. |
| 4,454,091 A | 6/1984 | Chion et al. |
| 4,455,709 A | 6/1984 | Zanini |
| 4,458,629 A | 7/1984 | Gerber |
| 4,480,061 A | 10/1984 | Coughlin et al. |
| 4,481,701 A | 11/1984 | Hewitt |
| 4,491,553 A | 1/1985 | Yamada et al. |
| 4,503,115 A | 3/1985 | Hemels et al. |
| 4,505,869 A | 3/1985 | Nishibori |
| 4,506,037 A | 3/1985 | Suzuki et al. |
| 4,508,595 A | 4/1985 | Gasland |
| 4,520,530 A | 6/1985 | Pinto |
| 4,551,294 A | 11/1985 | Wottka et al. |
| 4,559,376 A | 12/1985 | Kubat |
| 4,562,218 A | 12/1985 | Fornadel et al. |
| 4,584,357 A | 4/1986 | Harding |
| 4,594,372 A | 6/1986 | Natov et al. |
| 4,597,928 A | 7/1986 | Terentiev et al. |
| 4,608,922 A | 9/1986 | Pohl |
| 4,610,900 A | 9/1986 | Nishibori |
| 4,624,890 A | 11/1986 | Lloyd et al. |
| 4,632,170 A | 12/1986 | Pohl |
| 4,645,631 A | 2/1987 | Hegenstaller et al. |
| 4,659,754 A | 4/1987 | Edwards et al. |
| 4,663,225 A | 5/1987 | Farley et al. |
| 4,674,414 A | 6/1987 | Nülle et al. |
| 4,686,251 A | 8/1987 | Ostermann et al. |
| 4,687,793 A | 8/1987 | Motegi et al. |
| 4,713,291 A | 12/1987 | Sasaki et al. |
| 4,716,062 A | 12/1987 | Klein |
| 4,717,742 A | 1/1988 | Beshay |
| 4,717,743 A | 1/1988 | Wakabayashi et al. |
| 4,734,236 A | 3/1988 | Davis |
| 4,737,532 A | 4/1988 | Fujita et al. |
| 4,738,723 A | 4/1988 | Frizzell et al. |
| 4,746,688 A | 5/1988 | Bistak et al. |
| 4,769,109 A | 9/1988 | Tellvik et al. |
| 4,769,274 A | 9/1988 | Tellvik et al. |
| 4,791,020 A | 12/1988 | Kokta |
| 4,810,445 A | 3/1989 | Lamb, Sr. et al. |
| 4,818,604 A | 4/1989 | Tock |
| 4,833,181 A | 5/1989 | Narukawa et al. |
| 4,851,458 A | 7/1989 | Hopperdietzel |
| 4,865,788 A | 9/1989 | Davis |
| 4,874,095 A | 10/1989 | Warych |
| 4,894,192 A | 1/1990 | Warych |
| 4,911,700 A | 3/1990 | Makoui et al. |
| 4,915,764 A | 4/1990 | Miani |
| 4,927,579 A | 5/1990 | Moore |
| 4,929,498 A | 5/1990 | Suskind et al. |
| 4,935,182 A | 6/1990 | Ehner et al. |
| 4,944,734 A | 7/1990 | Wallach |
| 4,960,548 A | 10/1990 | Ikeda et al. |
| 4,963,603 A | 10/1990 | Felegi, Jr. et al. |
| 4,968,463 A | 11/1990 | Levasseur |
| 4,973,440 A | 11/1990 | Tamura et al. |
| 4,978,489 A | 12/1990 | Radvan et al. |
| 4,988,478 A | 1/1991 | Held |
| 5,002,713 A | 3/1991 | Palardy et al. |
| 5,008,310 A | 4/1991 | Beshay |
| 5,009,586 A | 4/1991 | Pallmann |
| 5,017,319 A | 5/1991 | Shen |
| 5,028,266 A | 7/1991 | Rettenmaier |
| 5,057,167 A | 10/1991 | Gersbeck |
| 5,064,692 A | 11/1991 | Hofmann et al. |
| 5,075,057 A | 12/1991 | Hoedl |
| 5,075,359 A | 12/1991 | Castagna et al. |
| 5,082,605 A | 1/1992 | Brooks et al. |
| 5,084,135 A | 1/1992 | Brooks et al. |
| 5,087,400 A | 2/1992 | Theuveny |
| 5,088,910 A | 2/1992 | Goforth et al. |
| 5,093,058 A | 3/1992 | Harmon et al. |
| 5,096,406 A | 3/1992 | Brooks et al. |
| 5,100,545 A | 3/1992 | Brooks |
| 5,100,603 A | 3/1992 | Neefe |
| 5,102,055 A | 4/1992 | Buschmann et al. |
| 5,104,411 A | 4/1992 | Makoui et al. |
| 5,120,776 A | 6/1992 | Raj et al. |
| 5,124,519 A | 6/1992 | Roy et al. |
| 5,134,023 A | 7/1992 | Hsu |
| 5,137,668 A | 8/1992 | Lamb, Sr. |
| 5,155,147 A | 10/1992 | Dietz et al. |
| 5,164,432 A | 11/1992 | Dehennau et al. |
| 5,183,837 A | 2/1993 | Lepori et al. |
| 5,194,461 A | 3/1993 | Bergquist et al. |
| 5,213,021 A | 5/1993 | Goforth et al. |
| 5,254,617 A | 10/1993 | Inoue et al. |
| 5,268,074 A | 12/1993 | Brooks et al. |
| 5,277,758 A | 1/1994 | Brooks et al. |
| 5,284,610 A | 2/1994 | Tai |
| 5,285,973 A | 2/1994 | Goforth et al. |
| 5,298,102 A | 3/1994 | Pohl |
| 5,331,087 A | 7/1994 | Menges |
| 5,350,370 A | 9/1994 | Jackson et al. |
| 5,351,895 A | 10/1994 | Brooks et al. |
| 5,366,790 A | 11/1994 | Liebel |
| 5,372,878 A | 12/1994 | Saito |
| 5,374,474 A | 12/1994 | Pratt et al. |
| 5,380,180 A | 1/1995 | Lamb, Sr. |
| 5,406,768 A | 4/1995 | Giuseppe et al. |
| 5,416,139 A | 5/1995 | Zeiszler |
| 5,421,205 A | 6/1995 | Pohl |
| 5,432,000 A | 7/1995 | Young, Sr. et al. |
| 5,437,766 A | 8/1995 | Van Phan et al. |
| 5,439,542 A | 8/1995 | Liebel |
| 5,439,749 A | 8/1995 | Klasell et al. |
| 5,441,801 A | 8/1995 | Deaner et al. |
| 5,480,602 A | 1/1996 | Nagaich |
| 5,486,553 A | 1/1996 | Deaner et al. |
| 5,497,594 A | 3/1996 | Giuseppe et al. |
| 5,498,478 A | 3/1996 | Hansen et al. |
| 5,516,472 A | 5/1996 | Laver |
| 5,516,585 A | 5/1996 | Young, Sr. et al. |
| 5,518,677 A | 5/1996 | Deaner et al. |
| 5,539,027 A | 7/1996 | Deaner et al. |
| 5,540,244 A | 7/1996 | Brooks et al. |
| 5,543,205 A | 8/1996 | Liebel |
| 5,547,745 A | 8/1996 | Hansen et al. |
| 5,558,933 A | 9/1996 | Anthony |
| 5,571,618 A | 11/1996 | Hansen et al. |
| 5,574,094 A | 11/1996 | Malucelli et al. |
| 5,582,682 A | 12/1996 | Ferretti |
| 5,582,847 A | 12/1996 | Peterson et al. |

| | | | | | | |
|---|---|---|---|---|---|---|
| 5,585,150 | A | 12/1996 | Sheehan | 6,821,614 B1 | 11/2004 | Dubelsten et al. |
| 5,585,155 | A | 12/1996 | Heikkila et al. | 6,824,729 B2 | 11/2004 | Oin et al. |
| 5,614,570 | A | 3/1997 | Hansen et al. | 6,855,182 B2 | 2/2005 | Sears |
| 5,618,858 | A | 4/1997 | Hauschildt et al. | 6,969,781 B2 | 11/2005 | Graef et al. |
| 5,643,359 | A | 7/1997 | Soroushian et al. | 2002/0010229 A1 | 1/2002 | Medoff et al. |
| 5,643,635 | A | 7/1997 | Ahn et al. | 2002/0019614 A1 | 2/2002 | Woon et al. |
| 5,663,216 | A | 9/1997 | Tomka | 2003/0021915 A1 | 1/2003 | Rohatgi et al. |
| 5,682,015 | A | 10/1997 | Harben | 2003/0032702 A1 | 2/2003 | Medoff et al. |
| 5,695,874 | A | 12/1997 | Deaner et al. | 2003/0100634 A1 | 5/2003 | Heath et al. |
| 5,746,958 | A | 5/1998 | Gustafsson et al. | 2003/0121380 A1 | 7/2003 | Cowell et al. |
| 5,759,680 | A | 6/1998 | Brooks et al. | 2003/0125688 A1 | 7/2003 | Keane et al. |
| 5,767,177 | A | 6/1998 | Omente et al. | 2003/0187102 A1 | 10/2003 | Medoff et al. |
| 5,773,138 | A | 6/1998 | Seethamraju et al. | 2003/0207064 A1 | 11/2003 | Bunyan et al. |
| 5,791,262 | A | 8/1998 | Knight et al. | 2004/0005461 A1 | 1/2004 | Nagle et al. |
| 5,819,491 | A | 10/1998 | Davis | 2004/0072924 A1 | 4/2004 | Sigworth et al. |
| 5,824,246 | A | 10/1998 | Reetz | | | |
| 5,827,607 | A | 10/1998 | Deaner et al. | | | |
| 5,851,469 | A | 12/1998 | Muller et al. | FOREIGN PATENT DOCUMENTS | | |
| 5,876,641 | A | 3/1999 | LeClair et al. | DE 43 31 747 | 3/1995 | |
| 5,882,564 | A | 3/1999 | Puppin | EP 0 161 766 A1 | 11/1985 | |
| 5,932,334 | A | 8/1999 | Deaner et al. | EP 0 330 729 A1 | 9/1988 | |
| 5,948,505 | A | 9/1999 | Puppin | EP 0 409 525 A2 | 7/1990 | |
| 5,948,524 | A | 9/1999 | Seethamraju et al. | JP 60-168611 | 2/1985 | |
| 5,952,105 | A | 9/1999 | Medoff et al. | JP 2171953 | 9/1986 | |
| 5,973,035 | A | 10/1999 | Medoff et al. | JP 61-273805 | 2/1988 | |
| 5,981,067 | A | 11/1999 | Seethamraju et al. | JP 63-033441 | 2/1988 | |
| 5,985,429 | A | 11/1999 | Plummer et al. | JP 63-033442 | 2/1988 | |
| 6,004,668 | A | 12/1999 | Deaner et al. | JP 63-033448 | 2/1988 | |
| 6,007,656 | A | 12/1999 | Heikkila et al. | WO WO 92/07022 | 10/1991 | |
| 6,015,611 | A | 1/2000 | Deaner et al. | WO WO 95/08954 | 3/1995 | |
| 6,015,612 | A | 1/2000 | Deaner et al. | WO WO 96/13468 | 5/1996 | |
| 6,054,207 | A | 4/2000 | Finley | WO WO 96/13551 | 5/1996 | |
| 6,085,923 | A | 7/2000 | Yaniger | WO WO 97/06942 | 2/1997 | |
| 6,106,944 | A | 8/2000 | Heikkila et al. | WO WO 97/18173 | 5/1997 | |
| 6,117,924 | A | 9/2000 | Brandt | WO WO 99/11453 | 3/1999 | |
| 6,122,877 | A | 9/2000 | Hendrickson et al. | WO WO 99/23138 | 5/1999 | |
| 6,180,257 | B1 | 1/2001 | Brandt et al. | WO WO 00/29183 | 5/2000 | |
| 6,200,682 | B1 | 3/2001 | Dubelsten et al. | WO WO 00/34567 | 6/2000 | |
| 6,207,729 | B1 | 3/2001 | Medoff et al. | WO WO 02/14039 A1 | 2/2002 | |
| 6,210,792 | B1 | 4/2001 | Seethamraju et al. | | | |
| 6,258,876 | B1 | 7/2001 | Medoff et al. | | | |
| 6,265,037 | B1 | 7/2001 | Godavarti et al. | OTHER PUBLICATIONS | | |
| 6,270,883 | B1 | 8/2001 | Sears et al. | | | |
| 6,270,893 | B1 | 8/2001 | Young, Sr. et al. | | | |
| 6,284,098 | B1 | 9/2001 | Jacobsen | | | |
| 6,337,138 | B1 | 1/2002 | Zehner et al. | | | |
| 6,344,268 | B1 | 2/2002 | Stucky et al. | | | |
| 6,346,160 | B1 | 2/2002 | Puppin | | | |
| 6,357,197 | B1 | 3/2002 | Serino et al. | | | |
| 6,409,952 | B1 | 6/2002 | Hacker et al. | | | |
| 6,420,626 | B1 | 7/2002 | Erspamer et al. | | | |
| 6,425,979 | B1 | 7/2002 | Hansen et al. | | | |
| 6,448,307 | B1 | 9/2002 | Medoff et al. | | | |
| 6,479,002 | B1 | 11/2002 | Becker et al. | | | |
| 6,495,225 | B1 | 12/2002 | Nakajima et al. | | | |
| 6,511,757 | B1 | 1/2003 | Brandt et al. | | | |
| 6,521,087 | B2 | 2/2003 | Hansen et al. | | | |
| 6,605,245 | B1 | 8/2003 | Dubelsten et al. | | | |
| 6,617,376 | B2 | 9/2003 | Korney, Jr. et al. | | | |
| 6,620,503 | B2 | 9/2003 | Qin et al. | | | |
| 6,632,863 | B2 | 10/2003 | Hutchison et al. | | | |
| 6,638,612 | B2 | 10/2003 | Jones | | | |
| 6,670,035 | B2 | 12/2003 | Pittman et al. | | | |
| 6,680,090 | B2 | 1/2004 | Godavarti et al. | | | |
| 6,682,789 | B2 | 1/2004 | Godavarti et al. | | | |
| 6,685,858 | B2 | 2/2004 | Korney, Jr. et al. | | | |
| 6,692,825 | B2 | 2/2004 | Qin et al. | | | |
| 6,730,249 | B2 | 5/2004 | Sears et al. | | | |
| 6,743,507 | B2 | 6/2004 | Barlow et al. | | | |
| 6,746,976 | B1 | 6/2004 | Urankar et al. | | | |
| 6,758,996 | B2 | 7/2004 | Monovoukas et al. | | | |
| 6,780,359 | B1 | 8/2004 | Zehner et al. | | | |
| 6,784,230 | B1 | 8/2004 | Patterson et al. | | | |

Klason et al., "The Efficiency of Cellulosic Fillers in Common Thermoplastics. Part I. Filling Without Processing Aids or Coupling Agents", International Journal of Polymeric Materials, Mar. 1984, pp. 159-187.

Kokta et al., "Composites of Poly(Vinyl Chloride) and Wood Fibers. Part II: Effect of Chemical Treatment", Polymer Composites, Apr. 1990, vol. 11, No. 2, pp. 84-89.

Kokta et al., "Composites of Polyvinyl Chloride-Wood Fibers. I. Effect of Isocyanate as a Bonding Agent", Polym. Plast. Technol. Eng. 29(1&2), 1990, pp. 87-118.

Kokta et al., "Composites of Polyvinyl Chloride-Wood Fibers. III. Effect of Silane as Coupling Agent", Journal of Vinyl Technology, Sep. 1990, vol. 12, No. 3, pp. 146-153.

Kokta et al., "Use of Wood Fibers in Thermoplastic Composites", Polymer Composites, Oct. 1983, vol. 4, No. 4, pp. 229-232.

Maldas et al., "Composites of Polyvinyl Chloride-Wood Fibers: IV. Effect of the Nature of Fibers". Journal of Vinyl Technology, Jun. 1989, vol. 11, No. 2, pp. 90-98.

Raj et al., "Use of Wood Fibers as Filler in Common Thermoplastic Studies on Mechanical Properties", Science and Engineering of Composite Materials, vol. 1, No. 3, 1989, pp. 85-98.

Raj et al., "Use of Wood Fibers in Thermoplastics. VII. The Effect of Coupling Agents in Polyethylene-Wood Fiber Composites", Journal of Applied Polymer Science, vol. 37, (1989), pp. 1089-1103.

Rogalski et al., "Poly(Vinyl-Chloride) Wood Fiber Composites", Antec '87, pp. 1436-1441.

Woodhams et al., "Wood Fibers as Reinforcing Fillers for Polyolefins", Polymer Engineering and Science, Oct. 1984, vol. 24, No. 15, pp. 1166-1171.

Yam et al., "Composites From Compounding Wood Fibers With Recycled High Density Polyethylene", Polymer Engineering and Science, Mid-Jun. 1990, vol. 30, No. 11, pp. 693-699.

Zadorecki et al., "Future Prospects for Wood Cellulose as Reinforcement in Organic Polymer Composites", Polymer Composites, Apr. 1989, vol. 10, No. 2, pp. 69-77.

Supplementary European Search Report, EP 03 71 1572, Feb. 28, 2005.

Abstract of JP 09213296, filed Feb. 5, 1996, in Chemical Abstracts 127:223004.

Abstract of JP 09267441, filed Oct. 14, 1997, in Chemical Abstracts 127:294599.

Abstract of (Doctorate) Dissertation Abstract Int. B1988, 58(9), 4962 (published in Sep. 1997), in Chemical Abstracts 128:128805.

COMPOSITIONS AND COMPOSITES OF CELLULOSIC AND LIGNOCELLULOSIC MATERIALS AND RESINS, AND METHODS OF MAKING THE SAME

CROSS-REFERENCE TO RELATED APPLICATIONS

This application is a continuation of U.S. Ser. No. 12/040,275, filed Feb. 29, 2008, and now abandoned, which is a divisional (and claims the benefit of priority under 35 U.S.C. §120) of U.S. Ser. No. 10/994,846, filed Nov. 22, 2004, and now abandoned, which is a divisional of U.S. application Ser. No. 10/336,972, filed Jan. 6, 2003, and now abandoned, which is a continuation-in-part of U.S. patent application Ser. No. 10/104,414, filed Mar. 21, 2002 and now abandoned. Each of these applications is incorporated by reference in its entirety.

BACKGROUND OF THE INVENTION

The invention relates to texturized cellulosic or lignocellulosic materials and compositions and composites made from such texturized materials.

Cellulosic and lignocellulosic materials are produced, processed, and used in large quantities in a number of applications. Once used, these materials are usually discarded. As a result, there is an ever-increasing amount of waste cellulosic and lignocellulosic material.

SUMMARY OF THE INVENTION

In general, the invention features texturized cellulosic or lignocellulosic materials and compositions and composites made therefrom.

In one embodiment, the features a process for manufacturing a composite. The method includes the steps of (a) shearing cellulosic or lignocellulosic fiber to the extent that its internal fibers are substantially exposed to form texturized cellulosic or lignocellulosic fiber, and (b) combining the cellulosic or lignocellulosic fiber with a resin. These steps can be carried out in any order (i.e., (a) then (b), or (b) then (a)) or concurrently (i.e., at around the same time). The resin can be, for example, a thermoplastic resin, a thermosetting resin, an elastomer, a tar, an asphalt, or a lignin. Specific examples include polystyrene, polycarbonate, polybutylene, thermoplastic polyester, polyether, thermoplastic polyurethane, PVC, Nylon, alkyd, diallyl phthalate, epoxy, melamine, phenolic, silicone, urea, thermosetting polyester, natural rubber, isoprene rubber, styrene-butadiene copolymers, neoprene, nitrile rubber, butyl rubber, ethylene propylene copolymer (i.e., "EPM"), ethylene propylene diene terpolymer (i.e., "EPDM"), hypalon, acrylic rubber, polysulfide rubber, silicones, urethanes, fluoroelastomers, butadiene, or epichlorohydrin rubber.

The fiber can be, for example, jute, kenaf, flax, hemp, cotton, rag, paper, paper products, or byproducts of paper manufacturing. Specific examples include pulp board, newsprint, magazine paper, poly-coated paper, and bleached kraft board. The fiber can be a natural or synthetic celluosic or lignocellulosic material, and can be woven or non-woven material.

The shearing step can be carried out using a rotary cutter or other mechanical method prior to combining with resin, or can be carried out in situ in a compounding machine or extruder. In some cases, a screw in the compounding machine or extruder can be effective for shearing the material.

In certain embodiments, the method can also include, after step (a) but prior to step (b), densifying the texturized fiber. The densification step increases the bulk density of the texturized material, generally by a factor of at least two or three. In some cases, the bulk density can be increased by a factor of five to ten or more. A preferred range of bulk densities for the densified texturized fiber is about 5-25 pounds per cubic foot. A more preferred range is about 8-15 pounds per cubic foot. The densification step can result in the compression of the texturized fiber into pellets of any shape or size.

The composite manufactured by the above methods is also an aspect of the invention. In a typical composite of the invention, at least about 50% of the fibers have a length/diameter ratio of at least about 5 (e.g., 5, 10, 15, 25, 30, 35, 40, 50, or more)

A composition that includes such composites, together with a chemical or chemical formulation, is also an aspect of the invention. Examples of such chemical formulations include compatibilizers such as FUSABOND® that allow for blending, bonding, adhesion, interphasing, and/or interfacing between otherwise incompatible materials such as hydrophilic fibers and hydrophobic resins.

In another embodiment, the invention features a process for preparing a texturized fibrous material. The process involves shearing a cellulosic or lignocellulosic material having internal fibers (e.g., flax; hemp; cotton; jute; rags; finished or unfinished paper, paper products, including poly-coated paper, or byproducts of paper manufacturing such as pulp board; or synthetic cellulosic or lignocellulosic materials such as rayon), to the extent that the internal fibers are substantially exposed, resulting in texturized fibrous material. The cellulosic or lignocellulosic material can be a woven material such as a woven fabric, or a non-woven material such as paper or bathroom tissue. The exposed fibers of the texturized fibrous material can have a length/diameter (L/D) ratio of at least about 5 (at least about 5, 10, 25, 50, or more). For example, at least about 50% of the fibers can have L/D ratios of this magnitude.

In another embodiment, the invention features a texturized fibrous material that includes a cellulosic or lignocellulosic material having internal fibers, where the cellulosic or lignocellulosic material is sheared to the extent that the internal fibers are substantially exposed.

The texturized fibrous material can, for example, be incorporated into (e.g., associated with, blended with, adjacent to, surrounded by, or within) a structure or carrier (e.g., a netting, a membrane, a flotation device, a bag, a shell, or a biodegradable substance). Optionally, the structure or carrier may itself be made from a texturized fibrous material (e.g., a texturized fibrous material of the invention), or of a composition or composite of a texturized fibrous material.

The texturized fibrous material can have a bulk density less than about 0.5 grams per cubic centimeter, or even less than about 0.2 g/cm$^3$.

Compositions that include the texturized fibrous materials described above, together with a chemical or chemical formulation (e.g., a pharmaceutical such as an antibiotic or contraceptive, optionally with an excipient; an agricultural compound such as a fertilizer, herbicide, or pesticide; or a formulation that includes enzymes) are also within the scope of the invention, as are compositions that include the texturized fibrous materials and other liquid or solid ingredients (e.g., particulate, powdered, or granulated solids such as plant seed, foodstuffs, or bacteria).

Composites that include thermoplastic resin and the texturized fibrous materials are also contemplated. The resin can be, for example, polyethylene, polypropylene, polystyrene, polycarbonate, polybutylene, a thermoplastic polyester, a polyether, a thermoplastic polyurethane, polyvinylchloride, or a polyamide, or a combination of two or more resins.

In some cases, at least about 5% by weight (e.g., 5%, 10%, 25%, 50%, 75%, 90%, 95%, 99%, or about 100%) of the fibrous material included in the composites is texturized.

The composite may include, for example, about 30% to about 70% by weight resin and about 30% to about 70% by weight texturized fibrous material, although proportions outside of these ranges may also be used. The composites can be quite strong, in some cases having a flexural strength of at least about 6,000 to 10,000 psi.

In another embodiment, the invention features a composite including a resin, such as a thermoplastic resin, and at least about 2% by weight, more preferably at least about 5% by weight, texturized cellulosic or lignocellulosic fiber. The invention also features a composite that includes polyethylene and at least about 50% by weight texturized cellulosic or lignocellulosic fiber.

The invention further features composites, including a resin and cellulosic or lignocellulosic fiber, that have flexural strengths of at least about 3,000 psi, or tensile strengths of at least about 3,000 psi.

In addition, the invention features a process for manufacturing a composite; the process includes shearing cellulosic or lignocellulosic fiber to form texturized cellulosic or lignocellulosic fiber, then combining the texturized fiber with a resin. A preferred method includes shearing the fiber with a rotary knife cutter. The invention also features a process for manufacturing a composite that includes shearing cellulosic or lignocellulosic fiber and combining the fiber with a resin.

The composites described above can also include inorganic additives such as calcium carbonate, graphite, asbestos, wollastonite, mica, glass, fiber glass, chalk, talc, silica, ceramic, ground construction waste, tire rubber powder, carbon fibers, or metal fibers (e.g., stainless steel or aluminum). Such inorganic additives can represent, for example, about 0.5% to about 20% of the total weight of the composite.

The composites can be in the form of, for example, a pallet (e.g., an injection molded pallet), pipes, panels, decking materials, boards, housings, sheets, poles, straps, fencing, members, doors, shutters, awnings, shades, signs, frames, window casings, backboards, wallboards, flooring, tiles, railroad ties, forms, trays, tool handles, stalls, bedding, dispensers, staves, films, wraps, totes, barrels, boxes, packing materials, baskets, straps, slips, racks, casings, binders, dividers, walls, indoor and outdoor carpets, rugs, wovens, and mats, frames, bookcases, sculptures, chairs, tables, desks, art, toys, games, wharves, piers, boats, masts, pollution control products, septic tanks, automotive panels, substrates, computer housings, above- and below-ground electrical casings, furniture, picnic tables, tents, playgrounds, benches, shelters, sporting goods, beds, bedpans, thread, filament, cloth, plaques, trays, hangers, servers, pools, insulation, caskets, book covers, clothes, canes, crutches, and other construction, agricultural, material handling, transportation, automotive, industrial, environmental, naval, electrical, electronic, recreational, medical, textile, and consumer products. The composites can also be in the form of a fiber, filament, or film.

The terms "texturized cellulosic or lignocellulosic material" and "texturized fibrous material" as used herein, mean that the cellulosic or lignocellulosic material has been sheared to the extent that its internal fibers are substantially exposed. At least about 50%, more preferably at least about 70%, of these fibers have a length/diameter (L/D) ratio of at least 5, more preferably at least 25, or at least 50. An example of texturized cellulosic material is shown in FIG. 1.

The texturized fibrous materials of the invention have properties that render them useful for various applications. For example, the texturized fibrous materials have absorbent properties, which can be exploited, for example, for pollution control. The fibers are generally biodegradable, making them suitable, for example, for drug or chemical delivery (e.g., in the treatment of humans, animals, or in agricultural applications). The texturized fibrous materials can also be used to reinforce polymeric resins.

The term "thermosetting resin", as used herein, refers to plastics (e.g., organic polymers) that are cured, set, or hardened into a permanent shape. Curing is an irreversible chemical reaction typically involving molecular cross-linking using heat or irradiation (e.g., UV irradiation). Curing of thermosetting materials can be initiated or completed at, for example, ambient or higher temperatures. The cross-linking that occurs in the curing reaction is brought about by the linking of atoms between or across two linear polymers, resulting in a three-dimensional rigidified chemical structure.

Examples of thermosetting resins include, but are not limited to, silicones, alkyds, diallyl phthalates (allyls), epoxies, melamines, phenolics, certain polyesters, silicones, ureas, polyurethanes, polyolefin-based thermosetting resins such as TELENE™ (BF Goodrich) and METTON™ (Hercules).

The term "elastomer", as used herein, refers to macromolecular materials that rapidly return to approximate their initial dimensions and shape after deformation and subsequent release.

Examples of elastomers include, but are not limited to, natural rubber, isoprene rubber, styrene-butadiene copolymers, neoprene, nitrile rubber, butyl rubber, ethylene propylene copolymer (i.e., "EPM") and ethylene propylene diene terpolymer (i.e., "EPDM"), hypalon, acrylic rubber, polysulfide rubber, silicones, urethanes, fluoroelastomers, butadiene, and epichlorohydrin rubber.

The term "tar", as used herein, means a typically thick brown to black liquid mixture of hydrocarbons and their derivatives obtained by distilling wood, peat, coal, shale, or other vegetable or mineral materials. An example is coal tar, which is made by destructive distillation of bituminous coal or crude petroleum (e.g., containing naphthalene, toluene, quinoline, aniline, and cresols).

The term "lignin", as used herein, refers to an amorphous substance, mixture, or powder isolated from wood, plants, recycled wood or plant products, or as a byproduct of papermaking. In nature, lignins, together with cellulose, form the woody cell walls of plants and the cementing material between them. They are typically polymeric and may be distinguished from cellulose by (1) a higher carbon content than cellulose, and (2) the inclusion of propyl-benzene units, methoxyl groups, and/or hydroxyl groups. They are generally not hydrolyzed by acids but may be soluble in hot alkali and bisulfite, and may be readily oxidizable. Lignins can be recovered from the liquor that results from the sulfate or soda process of making cellulosic pulp, or from sulfite liquor. The term lignin thus includes sulfite lignin, or lignin-sulfonates.

The term "asphalt", as used herein, refers, for example, to an amorphous, solid, or semisolid mixture of hydrocarbons, brownish-black pitch, or bitumen, produced from the higher-boiling point minerals oils by the action of oxygen. Asphalts include both asphaltenes and carbenes. Asphalts are commonly used for paving, roofing, and waterproofing materials.

The new compositions have properties that render them useful for various applications. Compositions that include texturized fibrous material and matrices are, for example, strong, lightweight, and inexpensive.

Other advantages afforded by the texturized fibers include:

(1) Reduced densities of matrix materials such as elastomers and thermosetting resins.

(2) Higher impact resistance due to increased interfacial area between matrix and texturized fiber and increased energy absorbed when texturized fiber delaminates from matrices.

(3) Reduced surface friction.

(4) Higher lubricity surfaces.

(5) Enhanced tolerance for and compatibilization of both the hydrophobic and hydrophilic constituents in the matrices.

(6) Enhanced ability to custom tailor the properties of the composition for specific requirements.

The raw materials used to make the composites are available as virgin or recycled materials; for example, they may include discarded containers composed of resins, and waste cellulosic or lignocellulosic fiber.

Other features and advantages of the invention will be apparent from the following detailed description, and from the claims.

DETAILED DESCRIPTION OF THE INVENTION

Examples of cellulosic raw materials include paper and paper products such as newsprint, poly-coated paper, and effluent from paper manufacture; examples of lignocellulosic raw materials include wood, wood fibers, and wood-related materials, as well as materials derived from kenaf, grasses, rice hulls, bagasse, cotton, jute, other stem plants (e.g., hemp, flax, bamboo; both bast and core fibers), leaf plants (e.g., sisal, abaca), and agricultural fibers (e.g., cereal straw, corn cobs, rice hulls, and coconut hair). Aside from virgin raw materials, post-consumer, industrial (e.g., offal), and processing waste (e.g., effluent) can also be used as fiber sources.

Preparation of Texturized Fibrous Material

If scrap cellulosic or lignocellulosic materials are used, they should preferably be clean and dry, although the materials can alternatively be sheared after wetting, either with water, a solvent, a compatibilizer, or a resin. The raw material can be texturized using any one of a number of mechanical means, or combinations thereof. One method of texturizing includes first cutting the cellulosic or lignocellulosic material into ¼- to ½-inch pieces, if necessary, using a standard cutting apparatus. Counter-rotating screw shredders and segmented rotating screw shredders such as those manufactured by Munson (Utica, N.Y.) can also be used, as can a standard document shredder as found in many offices.

The cellulosic or lignocellulosic material can then be sheared with a rotary cutter, such as the one manufactured by Sprout, Waldron Companies, as described in Perry's Chem. Eng. Handbook, 6th Ed., at 8-29 (1984). Although other settings can be used, the spacing between the rotating knives and bed knives of the rotary cutter is typically set to 0.020" or less, and blade rotation is set to 750 rpm or more. The rotary cutter can be cooled to 100° C. or lower during the process, for example, using a water jacket.

The texturized material is passed through a discharge screen. Larger screens (e.g., up to 6 mm) can be used in large-scale production. The cellulosic or lignocellulosic feedstock is generally kept in contact with the blades of the rotary cutter until the fibers are pulled apart; smaller screens (e.g., 2 mm mesh) provide longer residence times and more complete texturization, but can result in lower length/diameter (L/D) aspect ratios. A vacuum drawer can be attached to the screen to maximize and maintain fiber length/diameter aspect ratio.

Figure 1:
FIG. 1 is a photograph of a texturized newspaper, magnified fifty times.

The texturized fibrous materials can be directly stored in sealed bags or may be dried at approximately 105° C. for 4-18 hours (e.g., until the moisture content is less than about 0.5%) immediately before use. FIG. 1 is an SEM photograph of texturized newspaper.

Alternative texturizing methods include stone grinding, mechanical ripping or tearing, and other methods whereby the material's internal fibers can be exposed (e.g., pin grinding, air attrition milling). Examples of such other methods can also include in situ shearing in a compounding machine used to mix the fibers with resin or in an extruder. The fibrous material can be, for example, added before, after, or concurrent with the addition of the resin, irrespective of whether the resin is in a solid form (e.g., powdered or pelletized) form or a liquid form (e.g., molten or in solution).

After the material has been texturized, it can optionally be "densified," or compacted, to facilitate transport, storage, handling, processing, and/or feeding into compounding or extruding equipment. Densification can be carried out using a roll mill (which can form pellets or other shapes), for example, or a pellet mill. Pelletizing machines used in agriculture, pharmaceuticals (e.g., "pilling" machines), metallurgy, and other industries can be used or adapted for use for densifying texturized fiber.

During densification, the bulk density of the texturized material is increased. For example, whereas virgin poly-coated paper might have a bulk density of about 13 pounds per cubic foot, and texturized poly-coated paper might have a bulk density of about 2-6 pounds per cubic foot (i.e., about 0.03-0.1 g/cc), the densified material derived therefrom can have a bulk density as high as 25 pounds per cubic foot using a pellet mill. Preferably, the bulk density of the densified fiber does not exceed the bulk density of the starting material. Thus, in the case of poly-coated paper having a bulk density of 13 pounds per cubic foot, the preferred bulk density for the densified texturized fiber will be in the vicinity of 10-12 pounds per cubic foot. A bulk density in this range can allow for a relatively high feed rate in an extrusion process (i.e., about 10 times greater than that of a material having a bulk density of 2.8) without destroying the integrity of the texturized fiber. The densified texturized fiber can be substituted for non-densified texturized fiber in many applications, because, even though the densified texturized fiber has a relatively high bulk density, once the densified fiber is fed into compounding, extrusion, or other processing devices, the fibers can readily re-"open" to re-expose the fibers.

Uses of Texturized Fibrous Material

Texturized fibrous materials and compositions and composites of such fibers with other chemicals and chemical formulations can be prepared to take advantage of the materials' properties. The materials can be used to absorb chemicals, for example, potentially absorbing many times their own weight. Thus, the materials could, for instance, be used to absorb spilled oil, or for clean up of environmental pollution, for example, in water, in the air, or on land. Similarly, the material's absorbent properties, together with its biodegradability, also make them useful for delivery of chemicals or chemical formulations. For example, the materials can be treated with solutions of enzymes or pharmaceuticals such as antibiotics, nutrients, or contraceptives, and any necessary excipients, for drug delivery (e.g., for treatment of humans or animals, or for use as or in animal feed and/or bedding), as well as with solutions of fertilizers, herbicides, or pesticides. The materials can optionally be chemically treated to enhance a specific absorption property. For example, the materials can be treated with silanes to render them lipophilic.

Compositions including texturized materials combined with liquids or particulate, powdered, or granulated solids can also be prepared. For example, texturized materials can be blended with seeds (i.e., with or without treatment with a solution of fertilizer, pesticides, etc.), foodstuffs, or bacteria (e.g., bacteria that digest toxins). The ratio of fibrous materials to the other components of the compositions will depend on the nature of the components and readily be adjusted for a specific product application.

In some cases, it may be advantageous to associate the texturized fibrous materials, or compositions or composites of such materials, with a structure or carrier such as a netting, a membrane, a flotation device, a bag, a shell, or a biodegradable substance. Optionally, the structure of carrier may itself be made of a texturized fibrous material (e.g., a material of the invention), or a composition or composite thereof.

Composites of Texturized Fibrous Material and Resin

Texturized fibrous materials can also be combined with resins to form strong, lightweight composites. Materials that have been treated with chemicals or chemical formulations, as described above, can similarly be combined with biodegradable or non-biodegradable resins to form composites, allowing the introduction of, for example, hydrophilic substances into otherwise hydrophobic polymer matrices. Alternatively, the composites including texturized fibrous materials and resin can be treated with chemicals or chemical formulations.

The texturized cellulosic or lignocellulosic material provides the composite with strength. The composite may include from about 10% to about 90%, for example from about 30% to about 70%, of the texturized cellulosic or lignocellulosic material by weight.

The resin encapsulates the texturized cellulosic or lignocellulosic material in the composites, and helps control the shape of the composites. The resin also transfers external loads to the fibrous materials and protects the fiber from environmental and structural damage. Composites can include, for example, about 10% to about 90%, more preferably about 30% to about 70%, by weight, of the resin.

Resins are used in a variety of applications, for example, in food packaging. Food containers made of resins are typically used once, and then discarded. Examples of resins that are suitably combined with texturized fibers include polyethylene (including, e.g., low density polyethylene and high density polyethylene), polypropylene, polystyrene, polycarbonate, polybutylene, thermoplastic polyesters (e.g., PET), polyethers, thermoplastic polyurethane, PVC, polyamides (e.g., nylon) and other resins. It is preferred that the resins have a low melt flow index. Preferred resins include polyethylene and polypropylene with melt flow indices of less than 3 g/10 min, and more preferably less than 1 g/10 min.

The resins can be purchased as virgin material, or obtained as waste materials, and can be purchased in pelletized or granulated form. One source of waste resin is used polyethylene milk bottles. If surface moisture is present on the pelletized or granulated resin, however, it should be dried before use.

The composites can also include coupling agents. The coupling agents help to bond the hydrophilic fibers to the hydrophobic resins. Examples of coupling agents include maleic anhydride modified polyethylenes, such those in the FUSABOND® (available from Dupont, Delaware) and POLYBOND® (available from Uniroyal Chemical, Connecticut) series. One suitable coupling agent is a maleic anhydride modified high-density polyethylene such as FUSABOND® MB 100D.

The composites can also contain additives known to those in the art of compounding, such as plasticizers, lubricants, antioxidants, opacifiers, heat stabilizers, colorants, flame-retardants, biocides, impact modifiers, photostabilizers, and antistatic agents.

The composites can also include inorganic additives such as calcium carbonate, graphite, asbestos, wollastonite, mica, glass, fiber glass, chalk, silica, talc, ceramic, ground construction waste, tire rubber powder, carbon fibers, or metal fibers (e.g., aluminum, stainless steel). When such additives are included, they are typically present in quantities of from about 0.5% up to about 20-30% by weight. For example, submicron calcium carbonate can be added to the composites of fiber and resin to improve impact modification characteristics or to enhance composite strength.

Preparation of Compositions

Compositions containing the texturized cellulosic or lignocellulosic materials and chemicals, chemical formulations, or other solids can be prepared, for example, in various immersion, spraying, or blending apparatuses, including, but not limited to, ribbon blenders, cone blenders, double cone blenders, and Patterson-Kelly "V" blenders.

For example, a composition containing 90% by weight texturized cellulosic or lignocellulosic material and 10% by weight ammonium phosphate or sodium bicarbonate can be prepared in a cone blender to create a fire-retardant material for absorbing oil.

Preparation of Composites of Texturized Fiber and Resin

Composites of texturized fibrous material and resin can be prepared as follows. A standard rubber/plastic compounding 2-roll mill is heated to 325-400° F. The resin (usually in the form of pellets or granules) is added to the heated roll mill. After about 5 to 10 minutes, the coupling agent is added to the roll mill. After another five minutes, the texturized cellulosic or lignocellulosic material is added to the molten resin/coupling agent mixture. The texturized material is added over a period of about 10 minutes.

The composite is removed from the roll mill, cut into sheets and allowed to cool to room temperature. It is then compression molded into plaques using standard compression molding techniques.

Alternatively, a mixer, such as a Banbury internal mixer, is charged with the ingredients. The ingredients are mixed, while the temperature is preferably maintained at less than about 190° C. The mixture can then be compression molded.

In another embodiment, the ingredients can be mixed in an extruder mixer, such as a twin-screw extruder equipped with co-rotating screws. The resin and the coupling agent are introduced at the extruder feed throat; the texturized cellulosic or lignocellulosic material is introduced about ⅓ of the way down the length of the extruder into the molten resin. The internal temperature of the extruder is preferably maintained at less than about 190° C., although higher temperatures (e.g., 270° C.) might be encountered during extrusion of certain profiles. At the output, the composite can be, for example, pelletized by cold strand cutting.

Alternatively, the mixture can first be prepared in a mixer, then transferred to an extruder.

In another embodiment, the composite can be formed into fibers, using fiber-forming techniques known to those in the art, or into filaments for knitting, warping, weaving, braiding, or making non-wovens. In a further embodiment, the composite can be made into a film.

Properties of the Composites of Texturized Fibrous Material and Resin

The resulting composites include a network of fibers, encapsulated within a resin matrix. The fibers form a lattice network, which provides the composite with strength. Since the cellulosic or lignocellulosic material is texturized, the amount of surface area available to bond to the resin is increased, in comparison to composites prepared with un-texturized cellulosic or lignocellulosic material. The resin binds to the surfaces of the exposed fibers, creating an intimate blend of the fiber network and the resin matrix. The intimate blending of the fibers and the resin matrix further strengthens the composites.

These compositions can also include inorganic additives such as calcium carbonate, graphite, asbestos, wollastonite, mica, glass, fiber glass, chalk, silica, talc, flame retardants such as alumina trihydrate or magnesium hydroxide, ground construction waste, tire rubber powder, carbon fibers, or metal fibers (e.g., aluminum, stainless steel). These additives may reinforce, extend, change electrical or mechanical or compatibility properties, and may provide other benefits. When such additives are included, they may be present in loadings by weight from below 1% to as high as 80%. Typical loadings ranges are between 0.5% and 50% by weight.

Polymeric and elastomeric compositions can also include coupling agents. The coupling agents help to bond the hydrophilic fibers of the texturized fibrous material to the resins.

The compositions having thermosetting or elastomer matrices can also contain additives known to those in the art of compounding, such as plasticizers; lubricants; antioxidants; opacifiers; heat stabilizers; colorants; impact modifiers; photostabilizers; biocides; antistatic agents; organic or inorganic flame retardants, biodegradation agents; and dispersants. Special fiber surface treatments and additives can be used when a specific formulation requires specific property improvement.

The following are non-limiting examples of compositions:

Thermosetting Resins: Compositions of texturized fibrous material and thermosetting resins can be prepared as bulk molding compounds (BMCs), sheet molding compounds (SMCs), or as other formulations.

Bulk molding compounds (BMCs) are materials made by combining a resin and chopped fibers in a dough mixer, then mixing until the fibers are well wetted and the material has the consistency of modeling clay. Most BMCs are based on polyesters, but vinyl esters and epoxies are sometimes used. A pre-weighed amount of the compound is placed in a compression mold, which is then closed and heated under pressure to cross-link the thermosetting polymer. Many electrical parts are made using BMC compounds and processing. Other applications include microwave dishes, tabletops, and electrical insulator boxes.

Sheet molding compounds (SMCs) are made by compounding a polyester resin with fillers, pigments, catalysts, mold release agents, and/or special thickeners that react with the polymer to greatly increase the viscosity. The resin mixture is spread onto a moving nylon film. The resin passes under feeders, which disperse the texturized fibers. A second film is placed on top, sandwiching the compound inside. The material then passes through rollers that help the resin to wet the fibers, and the material is rolled up. Prior to use, the nylon films are removed and the compound is molded.

Other techniques and preparation procedures can be used to prepare and cure thermosetting systems.

Elastomers: Compositions of texturized fibrous material and elastomers can be prepared by known methods. In one method, for example, the elastomer is added to a rubber/plastic compounding two-roll mill. After a couple of minutes, the other ingredients, including a vulcanizing agent, are added to the roll mill. Once the elastomer has been compounded, the texturized fibrous material is added to the roll mill. The texturized fibrous material is added over a period of about 10 minutes. The compounded material is removed from the roll mill and cut into sheets. It is then compression molded into the desired shape using standard compression molding techniques.

Alternatively, a mixer, such as a Banbury internal mixer or appropriate twin or single screw compounder can be used. If a Banbury mixer is used, the compounded mixture can, for example, be discharged and dropped onto a roll mill for sheeting. Single or twin-screw compounders produce a sheet as an extrudate. The mixture can then be compression molded. Likewise, single- or twin-screw compounders can extrude a shaped profile that can be directly vulcanized. The composition can be molded, extruded, compressed, cut, or milled.

Uses of the Composites of Texturized Fibrous Material and Resin

The resin/fibrous material composites can be used in a number of applications. The composites are strong and light weight; they can be used, for example, as wood substitutes. The resin coating renders the composites water-resistant, so they may be used in outdoor applications. For example, the composites may be used to make pallets, which are often stored outdoors for extended periods of time, wine staves, rowboats, furniture, skis, and oars. Many other uses are contemplated, including panels, pipes, decking materials, boards, housings, sheets, poles, straps, fencing, members, doors, shutters, awnings, shades, signs, frames, window casings, backboards, wallboards, flooring, tiles, railroad ties, forms, trays, tool handles, stalls, bedding, dispensers, staves, films, wraps, totes, barrels, boxes, packing materials, baskets, straps, slips, racks, casings, binders, dividers, walls, indoor and outdoor carpets, rugs, wovens, and mats, frames, bookcases, sculptures, chairs, tables, desks, art, toys, games, wharves, piers, boats, masts, pollution control products, septic tanks, automotive panels, substrates, computer housings, above- and below-ground electrical casings, furniture, picnic tables, tents, playgrounds, benches, shelters, sporting goods, beds, bedpans, thread, filament, cloth, plaques, trays, hangers, servers, pools, insulation, caskets, book covers, clothes, canes, crutches, and other construction, agricultural, material handling, transportation, automotive, industrial, environmental, naval, electrical, electronic, recreational, medical, textile, and consumer products. Numerous other applications are also envisioned. The composites may also be used, for example, as the base or carcass for a veneer product, or sandwiched between layers of paper or other material. Moreover, the composites can be, for example, surface treated, grooved, milled, shaped, imprinted, textured, compressed, punched, or colored.

The following examples illustrate certain embodiments and aspects of the present invention and not to be construed as limiting the scope thereof.

EXAMPLES

Example 1

Figure 3:
FIG. 3 is a photograph of a half-gallon polyboard juice carton.

A 1500-pound skid of virgin, half-gallon juice cartons made of poly-coated white kraft board was obtained from International Paper. One such carton is shown in FIG. 3. Each carton was folded flat.

The cartons were fed into a 3 hp Flinch Baugh shredder at a rate of approximately 15 to 20 pounds per hour. The shredder was equipped with two rotary blades, each 12" in length, two fixed blades, and a 0.3" discharge screen. The gap between the rotary and fixed blades was 0.10".

Figure 4:
FIG. 4 is a photograph of shredded half-gallon polyboard juice cartons.

A sample of the output from the shredder, consisting primarily of confetti-like pieces, about 0.1" to 0.5" in width and about 0.25" to 1" in length, is shown in FIG. 4. The shredder output was fed into a Thomas Wiley Mill Model 2D5 rotary cutter. The rotary cutter had four rotary blades, four fixed blades, and a 2 mm discharge screen. Each blade was approximately 2" long. The blade gap was set at 0.020".

Figure 2:
FIG. 2 is a photograph of texturized poly-coated paper, magnified fifty times.
Figure 5:
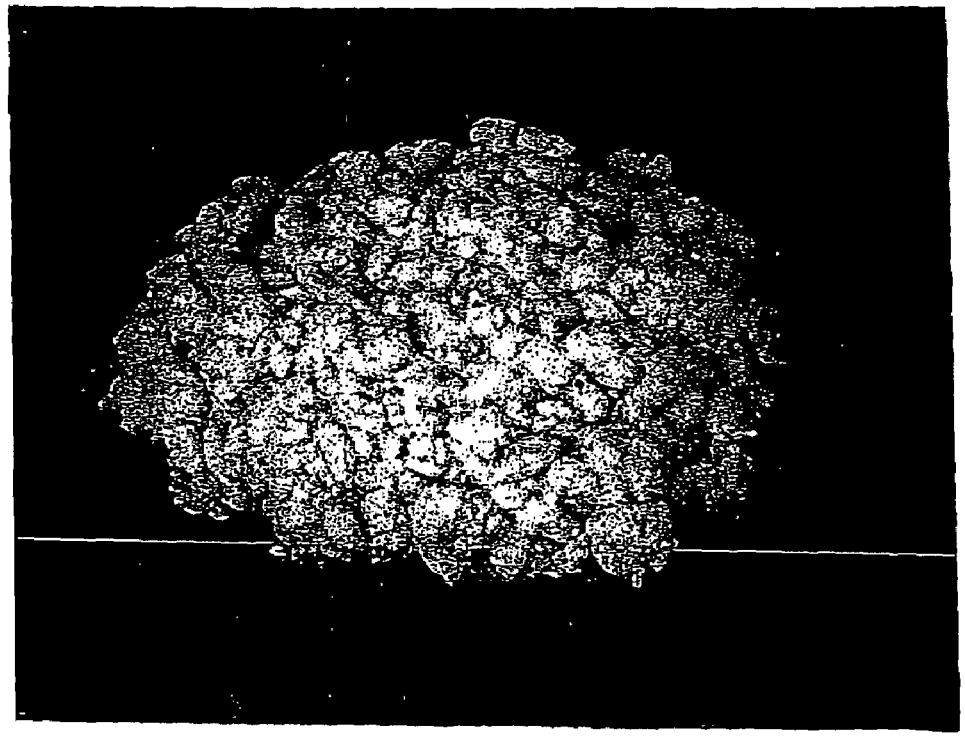
FIG. 5 is a photograph of texturized fibrous material prepared by shearing the shredded half-gallon polyboard juice cartons of FIG. 4.

The rotary cutter sheared the confetti-like pieces across the knife edges, tearing the pieces apart and releasing a finely texturized fiber at a rate of about one pound per hour. The fiber had an average minimum L/D ratio of between five and 100 or more. The bulk density of the texturized fiber was on the order of 0.1 g/cc. A sample of texturized fiber is shown in FIG. 5 at normal magnification, and in FIG. 2 at fifty-fold magnification.

Example 2

Composites of texturized fiber and resin were prepared as follows. A standard rubber/plastic compounding 2-roll mill was heated to 325-400° F. The resin (usually in the form of pellets or granules) was added to the heated roll mill. After about 5 to 10 minutes, the resin banded on the rolls (i.e., it melted and fused on the rolls). The coupling agent was then added to the roll mill. After another five minutes, the texturized cellulosic or lignocellulosic material was added to the molten resin/coupling agent mixture. The cellulosic or lignocellulosic fiber was added over a period of about 10 minutes.

The composite was then removed from the roll mill, cut into sheets, and allowed to cool to room temperature. Batches of about 80 g each were compression molded into 6"×6"×⅛" plaques using standard compression molding techniques.

One composition contained the following ingredients:

| Composition No. 1 | |
|---|---|
| Ingredient | Amount(g) |
| High density polyethylene[1] | 160 |
| Old newspaper[2] | 240 |
| Coupling agent[3] | 8 |

[1]Marlex 16007
[2]Texturized using rotary cutter with 2 mm mesh
[3]FUSABOND ® 100D The plaques were machined into appropriate test specimens and tested according to the procedures outlined in the method specified. Three different specimens were tested for each property, and the mean value for each test was calculated.

The properties of Composition No. 1 are as follows:

| | |
|---|---|
| Flexural strength ($10^3$ psi) | 9.81 (ASTM D790) |
| Flexural modulus ($10^5$ psi) | 6.27 (ASTM D790) |

A second composition contains the following ingredients:

| Composition No. 2 | |
|---|---|
| Ingredient | Amount(g) |
| High density polyethylene[1] | 160 |
| Old magazines[2] | 240 |
| Coupling agent[3] | 8 |

The properties of Composition No. 2 are as follows:

| | |
|---|---|
| Flexural strength ($10^3$ psi) | 9.06 (ASTM D790) |
| Flexural modulus ($10^5$ psi) | 6.78 (ASTM D790) |

A third composition contains the following ingredients:

| Composition No. 3 | |
|---|---|
| Ingredient | Amount(g) |
| HDPE[1] | 160 |
| Fiber paper[2] | 216 |
| 3.1 mm texturized kenaf | 24 |
| Coupling agent[3] | 8 |

The properties of Composition No. 3 are as follows:

| | |
|---|---|
| Flexural strength ($10^3$ psi) | 11.4 (ASTM D790) |
| Flexural modulus ($10^5$ psi) | 6.41 (ASTM D790) |

A fourth composition contains the following ingredients:

| Composition No. 4 | |
|---|---|
| Ingredient | Amount (g) |
| SUPERFLEX ® $CaCO_3$ | 33 |
| Fiber[2,4] | 67 |
| HDPE (w/3% compatibilizer)[1,3] | 100 |

[4]Virgin poly-coated milk cartons

The properties of Composition No. 4 are as follows:

| | | |
|---|---|---|
| Flexural strength ($10^5$ psi) | 8.29 | (ASTM D790) |
| Ultimate elongation (%) | <5 | (ASTM D638) |
| Flexural modulus ($10^5$ psi) | 10.1 | (ASTM D790) |
| Notch Izod (ft-lb/in) | 1.39 | (ASTM D256-97) |

A fifth composition contains the following ingredients:

| Composition No. 5 | |
| --- | --- |
| Ingredient | Amount (parts) |
| SUPERFLEX ® CaCO$_3$ | 22 |
| Fiber[2,4] | 67 |
| HDPE (w/3% compatibilizer)[1,3] | 100 |

The properties of Composition No. 5 are as follows:

| | | |
| --- | --- | --- |
| Flexural strength (10$^5$ psi) | 8.38 | (ASTM D790) |
| Ultimate elongation (%) | <5 | (ASTM D638) |
| Flexural modulus (10$^5$ psi) | 9.86 | (ASTM D790) |
| Notch Izod (ft-lb/in) | 1.37 | (ASTM D256-97) |

A sixth composition contains the following ingredients:

| Composition No. 6 | |
| --- | --- |
| Ingredient | Amount (parts) |
| ULTRAFLEX ® CaCO$_3$ | 33 |
| Fiber[2,4] | 67 |
| HDPE/compatibilizer[1,3] | 100 |

The properties of Composition No. 6 are as follows:

| | | |
| --- | --- | --- |
| Flexural strength (10$^5$ psi) | 7.43 | (ASTM D790) |
| Ultimate elongation (%) | <5 | (ASTM D638) |
| Flexural modulus (10$^5$ psi) | 11.6 | (ASTM D790) |
| Notch Izod (ft-lb/in) | 1.27 | (ASTM D256-97) |

A seventh composition contains the following ingredients:

| Composition No. 7 | |
| --- | --- |
| Ingredient | Amount (pbw) |
| HDPE (w/3% compatibilizer)[3,5] | 60 |
| Kraftboard[2] | 40 |

[5]HDPE with melt-flow index <1

The properties of Composition No. 7 are as follows:

| | | |
| --- | --- | --- |
| Flexural Strength (10$^5$ psi) | 7.79 | (ASTM D790) |
| Ultimate elongation (%) | <5 | (ASTM D638) |
| Flexural Modulus (10$^5$ psi) | 7.19 | (ASTM D790) |

Example 3

Foamed epoxies are used in thermal insulation applications where superior water resistance and elevated temperature properties are desired. Such epoxies can be reinforced with texturized fiber prepared according to the procedure in Example 3. Fillers such as calcium carbonate may optionally be used to obtain some cost reductions. However, overloading with filler can weaken the strength of the foam cell walls, particularly when the foam densities are in the range of five pounds per cubic foot or less, since such low foam density can result in thin, fragile walls within the foam. Filler loadings are generally in the four to five pounds/hundred weight (phr) of resin. Reinforcing with texturized fiber can also provide for reduced weight and cost. In addition, improved strength can be realized because of the high length-to-diameter (L/D) ratios of the texturized fiber. It is not unreasonable to employ up to 30 phr of the fiber.

A typical formulation includes:

| Ingredient | Parts |
| --- | --- |
| DGEBA (diglycidyl ether, of bisphenol A) | 100 |
| MPDA (m-phenylenediamine) | 10 |
| Celogen ® (p,p-oxybis-benzenesulfonylhydrazide) | 10 |
| (Uniroyal Chemical Company) | |
| Surfactant | 0.15 |
| Styrene Oxide | 5 |
| Texturized Fiber | 30 |

This formulation is mixed using standard epoxy mixing techniques. It produces a very high exotherm at the curing temperature of 120° C. and a foam density of about seven pounds per cubic foot.

Other embodiments are within the claims.

What is claimed is:

1. A process comprising:
re-opening a densified fibrous material, the densified fibrous material having been prepared by shearing a cellulosic or lignocellulosic material having internal fibers to an extent that the internal fibers have been substantially exposed, providing a material having a bulk density of less than about 0.5 g/cm$^3$, and then densifying the sheared material to increase the bulk density of the sheared material; and
blending the re-opened fibrous material with a bacteria.

2. The process of claim 1 wherein re-opening substantially re-exposes the fibers.

3. The process of claim 1 wherein the densified material has a bulk density that does not exceed a bulk density of the cellulosic or lignocellulosic material prior to physical treatment.

4. The process of claim 1 wherein the physically treated material has been compressed.

5. The process of claim 1 wherein the physically treated material has been stored in sealed bags.

6. The process of claim 1 further comprising treating the re-opened fibrous material with an enzyme solution.

7. The process of claim 1 wherein the cellulosic or lignocellulosic material is selected from the group consisting of paper, paper products, wood, wood fibers, kenaf, grasses, rice hulls, bagasse, cotton, jute, flax, hemp, stem plants, leaf plants, and agricultural fibers.

8. The process of claim 1 wherein the densified material has a bulk density of from about 5 to 25 pounds per cubic foot (0.08 to 0.40 g/cm3).

9. The process of claim 1 wherein the densified material has a bulk density of from about 8 to 15 pounds per cubic foot (0.13 to 0.24 g/cm3).

10. The process of claim 1 wherein the densified material has a bulk density of from about 10 to 12 pounds per cubic foot (0.16 to 0.19 g/cm3).

11. The process of claim 1 wherein densifying increases bulk density by a factor of at least two.

12. The process of claim 1 wherein densifying increases bulk density by a factor of three.

13. The process of claim 1 wherein densifying has been carried out using a roll mill.

14. The process of claim 1 wherein densifying has been carried out using a pellet mill.

15. The process of claim 1 wherein the densified material is in the form of pellets.

16. The process of claim 1 wherein the cellulosic or lignocellulosic material comprises waste paper.

17. A process comprising:
re-opening a densified fibrous material in the form of pellets, the densified fibrous material having been prepared by shearing a cellulosic or lignocellulosic material having internal fibers to an extent that the internal fibers have been substantially exposed, providing a material having a bulk density of less than about 0.5 g/cm$^3$, and then densifying the sheared material to increase the bulk density of the sheared material.

18. A process comprising:
re-opening a densified fibrous material, the densified fibrous material having been prepared by shearing a cellulosic or lignocellulosic material, the cellulosic or lignocellulosic material comprising waste paper and having internal fibers, to an extent that the internal fibers have been substantially exposed, providing a material having a bulk density of less than about 0.5 g/cm$^3$, and then densifying the sheared material to increase the bulk density of the sheared material.

19. The process of claim 18 wherein re-opening substantially re-exposes the fibers.

20. The process of claim 18 wherein the densified material has a bulk density that does not exceed a bulk density of the cellulosic or lignocellulosic material prior to physical treatment.

21. The process of claim 18 wherein the physically treated material has been compressed.

22. The process of claim 18 further comprising blending the re-opened fibrous material with a bacteria.

23. The process of claim 18 further comprising treating the re-opened fibrous material with an enzyme solution.

24. The process of claim 18 wherein the cellulosic or lignocellulosic material further comprises a material selected from the group consisting of wood, wood fibers, kenaf, grasses, rice hulls, bagasse, cotton, jute, flax, hemp, stem plants, leaf plants, and agricultural fibers.

25. The process of claim 18 wherein the densified material has a bulk density of from about 5 to 25 pounds per cubic foot (0.08 to 0.40 g/cm$^3$).

26. The process of claim 18 wherein densifying increases bulk density by a factor of at least two.

\* \* \* \* \*